(12) United States Patent
Sheets, Jr. et al.

(10) Patent No.: US 7,749,235 B2
(45) Date of Patent: Jul. 6, 2010

(54) STOMACH INVAGINATION METHOD AND APPARATUS

(75) Inventors: John Wesley Sheets, Jr., Bridgewater, NJ (US); Mark S. Ortiz, Milford, OH (US); Fredrick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 356 days.

(21) Appl. No.: 11/551,406

(22) Filed: Oct. 20, 2006

(65) Prior Publication Data

US 2008/0147112 A1 Jun. 19, 2008

(51) Int. Cl.
*A61B 17/10* (2006.01)
(52) U.S. Cl. ...................................... 606/139
(58) Field of Classification Search .................. 606/139
See application file for complete search history.

(56) References Cited

U.S. PATENT DOCUMENTS

| | | | |
|---|---|---|---|
| 3,994,764 A * | 11/1976 | Wolinski | 156/218 |
| 4,735,616 A | 4/1988 | Eibl et al. | |
| 4,766,898 A | 8/1988 | Hardy et al. | |
| 4,874,368 A | 10/1989 | Miller et al. | |
| 4,919,152 A | 4/1990 | Ger | |
| 5,004,469 A | 4/1991 | Palmieri et al. | |
| 5,154,320 A | 10/1992 | Bolduc | |
| 5,254,113 A | 10/1993 | Wilk | |
| 5,312,333 A | 5/1994 | Churinetz et al. | |
| 5,320,630 A * | 6/1994 | Ahmed | 606/140 |
| 5,324,305 A | 6/1994 | Kanner | |
| 5,372,585 A | 12/1994 | Tiefenbrun et al. | |
| 5,443,481 A | 8/1995 | Lee | |
| 5,474,540 A | 12/1995 | Miller et al. | |

(Continued)

FOREIGN PATENT DOCUMENTS

EP 0315222 B1 11/1992

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001.

(Continued)

*Primary Examiner*—(Jackie) Tan-Uyen T Ho
*Assistant Examiner*—Son Dang
(74) *Attorney, Agent, or Firm*—Frost Brown Todd LLC

(57) ABSTRACT

A system for creating an invaginated portion in a stomach comprises a suction device and a securing member. The suction device comprises a suction head operable to provide suction, a shaft connected to the suction head, and a vacuum lumen in fluid communication with the suction head. The suction head and vacuum lumen are operable to induce a vacuum adjacent to tissue. The suction device is further operable to create an invaginated portion with the tissue. The securing member is operable to substantially maintain the configuration of the invaginated portion of tissue. The suction device may comprise gripping jaw members having teeth. The securing member may comprise an adhesive and/or sutures and the like. The system may be used to create invaginated portions within a stomach. Such invaginated portions may reduce stomach volume to address obesity or other conditions.

13 Claims, 11 Drawing Sheets

U.S. PATENT DOCUMENTS

| | | | |
|---|---|---|---|
| 5,529,577 A | 6/1996 | Hammerslag | |
| 5,582,596 A | 12/1996 | Fukunaga et al. | |
| 5,605,541 A | 2/1997 | Holm | |
| 5,718,711 A | 2/1998 | Berenstein et al. | |
| 5,752,965 A | 5/1998 | Francis et al. | |
| 5,759,169 A | 6/1998 | Marx | |
| 5,759,171 A | 6/1998 | Coelho et al. | |
| 5,814,022 A | 9/1998 | Antanavich et al. | |
| 5,844,087 A | 12/1998 | Zimmerman et al. | |
| 5,895,412 A | 4/1999 | Tucker | |
| 5,928,611 A | 7/1999 | Leung | |
| 5,981,621 A | 11/1999 | Clark et al. | |
| 6,007,515 A | 12/1999 | Epstein et al. | |
| 6,010,714 A | 1/2000 | Leung et al. | |
| 6,055,828 A | 5/2000 | Rivera et al. | |
| 6,099,807 A | 8/2000 | Leung | |
| 6,113,571 A | 9/2000 | Zinger et al. | |
| 6,143,352 A | 11/2000 | Clark et al. | |
| 6,143,805 A | 11/2000 | Hickey et al. | |
| 6,162,239 A | 12/2000 | Manhes | |
| 6,174,919 B1 | 1/2001 | Hickey | |
| 6,183,593 B1 | 2/2001 | Narang et al. | |
| 6,206,905 B1 | 3/2001 | Holm et al. | |
| 6,217,603 B1 | 4/2001 | Clark et al. | |
| 6,228,051 B1 | 5/2001 | Trumbull | |
| 6,234,994 B1 | 5/2001 | Zinger | |
| 6,245,933 B1 | 6/2001 | Malofsky et al. | |
| 6,280,399 B1 | 8/2001 | Rossin et al. | |
| 6,283,933 B1 | 9/2001 | D'Alessio et al. | |
| 6,302,898 B1 | 10/2001 | Edwards et al. | |
| 6,306,243 B1 | 10/2001 | Clark et al. | |
| 6,310,166 B1 | 10/2001 | Hickey et al. | |
| 6,322,852 B1 | 11/2001 | Leung | |
| 6,325,810 B1 | 12/2001 | Hamilton et al. | |
| 6,340,097 B1 | 1/2002 | D'Alessio et al. | |
| 6,352,704 B1 | 3/2002 | Nicholson et al. | |
| 6,372,313 B1 | 4/2002 | D'Alessio et al. | |
| 6,376,019 B1 | 4/2002 | Leung | |
| 6,394,975 B1 | 5/2002 | Epstein | |
| 6,394,982 B1 | 5/2002 | Ehrenfels | |
| 6,398,797 B2 | 6/2002 | Bombard et al. | |
| 6,412,639 B1 | 7/2002 | Hickey | |
| 6,420,590 B1 | 7/2002 | Badejo et al. | |
| 6,425,704 B2 | 7/2002 | Voiers et al. | |
| 6,425,910 B1 * | 7/2002 | Hugueny et al. | 606/206 |
| 6,428,233 B1 | 8/2002 | Clark et al. | |
| 6,428,234 B1 | 8/2002 | Bobo et al. | |
| 6,432,084 B1 | 8/2002 | Levinson et al. | |
| 6,433,096 B1 | 8/2002 | Hickey et al. | |
| 6,439,789 B1 | 8/2002 | Balance et al. | |
| 6,454,739 B1 | 9/2002 | Chang | |
| 6,455,064 B1 | 9/2002 | Narang et al. | |
| 6,458,095 B1 | 10/2002 | Wirt et al. | |
| 6,461,361 B1 | 10/2002 | Epstein | |
| 6,461,367 B1 | 10/2002 | Kirsch et al. | |
| 6,464,663 B1 | 10/2002 | Zinger | |
| 6,468,520 B1 | 10/2002 | Rowe et al. | |
| 6,471,670 B1 | 10/2002 | Enrenfels et al. | |
| 6,478,191 B1 | 11/2002 | D'Alessio et al. | |
| 6,488,197 B1 | 12/2002 | Whitman | |
| 6,488,650 B1 | 12/2002 | Epstein et al. | |
| 6,488,944 B2 | 12/2002 | Narang | |
| 6,491,201 B1 | 12/2002 | Whitman | |
| 6,494,896 B1 | 12/2002 | D'Alessio et al. | |
| 6,512,023 B1 | 1/2003 | Malofsky et al. | |
| 6,527,749 B1 | 3/2003 | Roby et al. | |
| 6,540,716 B1 | 4/2003 | Holm | |
| 6,547,467 B2 | 4/2003 | Quintero | |
| 6,558,400 B2 * | 5/2003 | Deem et al. | 606/151 |
| 6,565,840 B1 | 5/2003 | Clark et al. | |
| 6,579,469 B1 | 6/2003 | Nicholson et al. | |
| 6,585,967 B2 | 7/2003 | Narang et al. | |
| 6,589,269 B2 | 7/2003 | Zhu et al. | |
| 6,592,281 B2 | 7/2003 | Clark et al. | |
| 6,595,940 B1 | 7/2003 | D'Alessio et al. | |
| 6,602,496 B2 | 8/2003 | Hedgpeth et al. | |
| 6,605,667 B1 | 8/2003 | Badejo et al. | |
| 6,607,631 B1 | 8/2003 | Badejo et al. | |
| 6,613,020 B1 | 9/2003 | Holm et al. | |
| 6,616,019 B2 | 9/2003 | D'Alessio et al. | |
| 6,620,846 B1 | 9/2003 | Jonn et al. | |
| 6,637,967 B2 | 10/2003 | Bobo et al. | |
| 6,663,639 B1 * | 12/2003 | Laufer et al. | 606/139 |
| 6,666,873 B1 | 12/2003 | Cassell | |
| 6,676,322 B1 | 1/2004 | Leung | |
| 6,681,979 B2 | 1/2004 | Whitman | |
| 6,695,199 B2 | 2/2004 | Whitman | |
| 6,705,790 B2 | 3/2004 | Quintero et al. | |
| 6,743,858 B2 | 6/2004 | Hickey et al. | |
| 6,746,667 B2 | 6/2004 | Badejo et al. | |
| 6,748,950 B2 | 6/2004 | Clark et al. | |
| 6,764,467 B1 | 7/2004 | Roby et al. | |
| 6,767,552 B2 | 7/2004 | Narang | |
| 6,779,657 B2 | 8/2004 | Mainwaring et al. | |
| 6,783,514 B2 | 8/2004 | Tovey et al. | |
| 6,802,416 B1 | 10/2004 | D'Alessio et al. | |
| 6,802,822 B1 | 10/2004 | Dodge | |
| 6,811,341 B2 | 11/2004 | Crane | |
| D500,085 S | 12/2004 | Cotter et al. | |
| 6,835,200 B2 * | 12/2004 | Laufer et al. | 606/153 |
| 6,837,027 B2 | 1/2005 | Hickey | |
| 6,863,660 B2 | 3/2005 | Marx | |
| 6,869,395 B2 * | 3/2005 | Page et al. | 600/127 |
| 6,884,232 B1 | 4/2005 | Hagmann et al. | |
| 6,896,684 B2 | 5/2005 | Monassevitch et al. | |
| 6,896,838 B2 | 5/2005 | D'Alessio | |
| 6,921,381 B2 | 7/2005 | Spero et al. | |
| 6,942,875 B2 | 9/2005 | Hedgpeth | |
| 6,960,040 B2 | 11/2005 | D'Alessio et al. | |
| 6,994,715 B2 * | 2/2006 | Gannoe et al. | 606/153 |
| 7,037,344 B2 | 5/2006 | Kagan et al. | |
| 7,083,629 B2 * | 8/2006 | Weller et al. | 606/151 |
| 7,153,314 B2 * | 12/2006 | Laufer et al. | 606/153 |
| 7,306,614 B2 * | 12/2007 | Weller et al. | 606/151 |
| 7,361,180 B2 * | 4/2008 | Saadat et al. | 606/139 |
| 2002/0012678 A1 | 1/2002 | Narang | |
| 2002/0037310 A1 | 3/2002 | Jonn et al. | |
| 2002/0048480 A1 | 4/2002 | D'Alessio et al. | |
| 2002/0055573 A1 | 5/2002 | Malofsky et al. | |
| 2002/0065336 A1 | 5/2002 | Hickey et al. | |
| 2002/0068946 A1 * | 6/2002 | Kortenbach et al. | 606/142 |
| 2002/0078967 A1 * | 6/2002 | Sixto et al. | 128/898 |
| 2002/0119184 A1 | 8/2002 | Nicholson et al. | |
| 2002/0147462 A1 | 10/2002 | Mair et al. | |
| 2002/0156203 A1 | 10/2002 | Hickey et al. | |
| 2002/0157675 A1 | 10/2002 | Clark et al. | |
| 2002/0165483 A1 | 11/2002 | Miller et al. | |
| 2002/0173770 A1 | 11/2002 | Flory et al. | |
| 2002/0176732 A1 | 11/2002 | Quintero et al. | |
| 2002/0176733 A1 | 11/2002 | Clark et al. | |
| 2002/0185396 A1 | 12/2002 | Mainwaring et al. | |
| 2002/0192011 A1 | 12/2002 | Bobo et al. | |
| 2002/0192107 A1 | 12/2002 | Hickey | |
| 2003/0007826 A1 | 1/2003 | Badejo et al. | |
| 2003/0007946 A1 | 1/2003 | Narang et al. | |
| 2003/0007947 A1 | 1/2003 | Narang | |
| 2003/0007948 A1 | 1/2003 | Hedgpeth | |
| 2003/0007949 A1 | 1/2003 | Hedgpeth et al. | |
| 2003/0015557 A1 | 1/2003 | D'Alessio et al. | |
| 2003/0023316 A1 * | 1/2003 | Brown et al. | 623/23.72 |
| 2003/0031499 A1 | 2/2003 | Heard et al. | |
| 2003/0032833 A1 | 2/2003 | Badejo et al. | |
| 2003/0039781 A1 | 2/2003 | D'Alessio et al. | |
| 2003/0044219 A1 | 3/2003 | Quintero | |

| | | | |
|---|---|---|---|
| 2003/0060380 A1 | 3/2003 | Ayarza et al. | |
| 2003/0063944 A1 | 4/2003 | Leung | |
| 2003/0080151 A1 | 5/2003 | D'Alessio et al. | |
| 2003/0082116 A1 | 5/2003 | Badejo et al. | |
| 2003/0096069 A1 | 5/2003 | D'Alessio | |
| 2003/0149128 A1 | 8/2003 | Malofsky et al. | |
| 2003/0181964 A1 | 9/2003 | Sharkey et al. | |
| 2003/0202956 A1 | 10/2003 | Clark et al. | |
| 2004/0026282 A1 | 2/2004 | D'Alessio et al. | |
| 2004/0059283 A1 | 3/2004 | Kirwan et al. | |
| 2004/0092892 A1* | 5/2004 | Kagan et al. | 604/264 |
| 2004/0111115 A1 | 6/2004 | Maw | |
| 2004/0120849 A1 | 6/2004 | Stewart et al. | |
| 2004/0122452 A1 | 6/2004 | Deem et al. | |
| 2004/0137067 A1 | 7/2004 | Narang et al. | |
| 2004/0143290 A1 | 7/2004 | Brightbill | |
| 2004/0151688 A1 | 8/2004 | Sherbondy et al. | |
| 2004/0162568 A1* | 8/2004 | Saadat et al. | 606/139 |
| 2004/0190975 A1 | 9/2004 | Goodman et al. | |
| 2004/0193184 A1* | 9/2004 | Laufer et al. | 606/139 |
| 2004/0193190 A1 | 9/2004 | Liddicoat et al. | |
| 2004/0223932 A1 | 11/2004 | Hedgpeth et al. | |
| 2004/0223946 A1 | 11/2004 | Kidd et al. | |
| 2004/0234578 A1 | 11/2004 | Chen et al. | |
| 2004/0254561 A1 | 12/2004 | Stenton | |
| 2005/0000646 A1* | 1/2005 | Ryan et al. | 156/314 |
| 2005/0021085 A1 | 1/2005 | Abrams et al. | |
| 2005/0033328 A1 | 2/2005 | Laufer et al. | |
| 2005/0042266 A1 | 2/2005 | Narang | |
| 2005/0047846 A1 | 3/2005 | Narang et al. | |
| 2005/0070935 A1 | 3/2005 | Ortiz | |
| 2005/0075653 A1* | 4/2005 | Saadat et al. | 606/139 |
| 2005/0096673 A1* | 5/2005 | Stack et al. | 606/151 |
| 2005/0145671 A1 | 7/2005 | Viola | |
| 2005/0147457 A1 | 7/2005 | Badejo et al. | |
| 2005/0149200 A1 | 7/2005 | Silverman et al. | |
| 2005/0175395 A1 | 8/2005 | Quintero et al. | |
| 2005/0182443 A1 | 8/2005 | Jonn et al. | |
| 2005/0184121 A1 | 8/2005 | Heinrich | |
| 2005/0192599 A1* | 9/2005 | Demarais | 606/151 |
| 2005/0220849 A1 | 10/2005 | Hickey | |
| 2005/0228446 A1 | 10/2005 | Mooradian et al. | |
| 2005/0230453 A1 | 10/2005 | Viola | |
| 2005/0256446 A1 | 11/2005 | Criscuolo et al. | |
| 2005/0261712 A1* | 11/2005 | Balbierz et al. | 606/153 |
| 2006/0009099 A1 | 1/2006 | Jonn et al. | |
| 2006/0195139 A1* | 8/2006 | Gertner | 606/201 |
| 2007/0276408 A1* | 11/2007 | Filipi et al. | 606/139 |
| 2008/0190989 A1* | 8/2008 | Crews et al. | 227/176.1 |

FOREIGN PATENT DOCUMENTS

| | | | |
|---|---|---|---|
| EP | 0716833 | A2 | 6/1996 |
| EP | 0648510 | B1 | 11/1998 |
| EP | 0669100 | B1 | 11/1998 |
| EP | 1078600 | A2 | 2/2001 |
| EP | 1159081 | A1 | 12/2001 |
| EP | 1381321 | A2 | 1/2004 |
| EP | 1113839 | B1 | 11/2004 |
| EP | 1073484 | B1 | 8/2005 |
| EP | 1411836 | B1 | 10/2005 |
| JP | 10262986 | | 10/1998 |
| JP | 2000217830 | | 8/2000 |
| JP | 2001157716 | | 6/2001 |
| JP | 2001190558 | | 7/2001 |
| JP | 2002233581 | | 8/2002 |
| JP | 2003126268 | | 5/2003 |
| JP | 2005028009 | | 2/2005 |
| JP | 2005169125 | | 6/2005 |
| WO | WO 92/09651 | | 6/1992 |
| WO | WO 95/31137 | A1 | 11/1995 |
| WO | WO 95/34244 | | 12/1995 |
| WO | WO 98/41154 | A1 | 9/1998 |
| WO | WO 99/17833 | A1 | 4/1999 |
| WO | WO 99/30629 | A1 | 6/1999 |
| WO | WO 01/12257 | A1 | 2/2001 |
| WO | WO 01/24869 | A1 | 4/2001 |
| WO | WO 01/62158 | A2 | 8/2001 |
| WO | WO 01/62162 | A1 | 8/2001 |
| WO | WO 01/62333 | A1 | 8/2001 |
| WO | WO 02/067785 | A2 | 9/2002 |
| WO | WO 03/088845 | | 10/2003 |

OTHER PUBLICATIONS

Ikeda, et al.; "Device for Applying Organism Tissue Adhesive;" published in Japan [translated abstract for Patent Application No. JP2000320375]; Jul. 17, 2001.

Gomibuchi, Makoto; "Medical Adhesive Applicator;" published in Japan [translated abstract for Patent Application No. JP11023146]; Aug. 8, 2000.

Ikeda, et al.; "Organism-Tissue Adhesive Applicator;" published in Japan [translated abstract for Patent Application No. JP2001033756]; Aug. 20, 2002.

Ikeda, et al.; "Biological Tissue Adhesive Applicator;" published in Japan [translated abstract for Patent Application No. JP2001323890]; May 7, 2003.

Arikawa, Seiki; "Biological Tissue Adhesive Applicator;" published in Japan [translated abstract for Patent Application No. JP2003273091]; Feb. 3, 2005.

Keller, Wilhelm A.; "Applicator for Dispensing Appliance;" published in Japan [translated abstract for Patent Application No. JP2004358509]; Jun. 30, 2005.

Sasaki, Hiroshi; "Adhesive Agent Applicator for Surgical Operation;" published in Japan [translated abstract for Patent Application No. JP09076817]; Oct. 6, 1998.

Search Report dated Feb. 25, 2008 for Application No. EP07254150.

European Search Report dated Feb. 25, 2008 for Application No. EP 07254150.

* cited by examiner

STOMACH INVAGINATION METHOD AND APPARATUS

BACKGROUND

Obesity has been a problem for many years. A variety of methods and devices have been used to try to address obesity in patients, including gastric bypasses and implanted devices. Biosurgical adhesives have also been used in a variety of ways in various medical procedures. An exemplary adhesive is disclosed in U.S. Pub. No. 2004/0190975, the disclosure of which is incorporated by reference herein. While several systems and methods have been made and used for addressing obesity, and while adhesives have been used in various other medical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
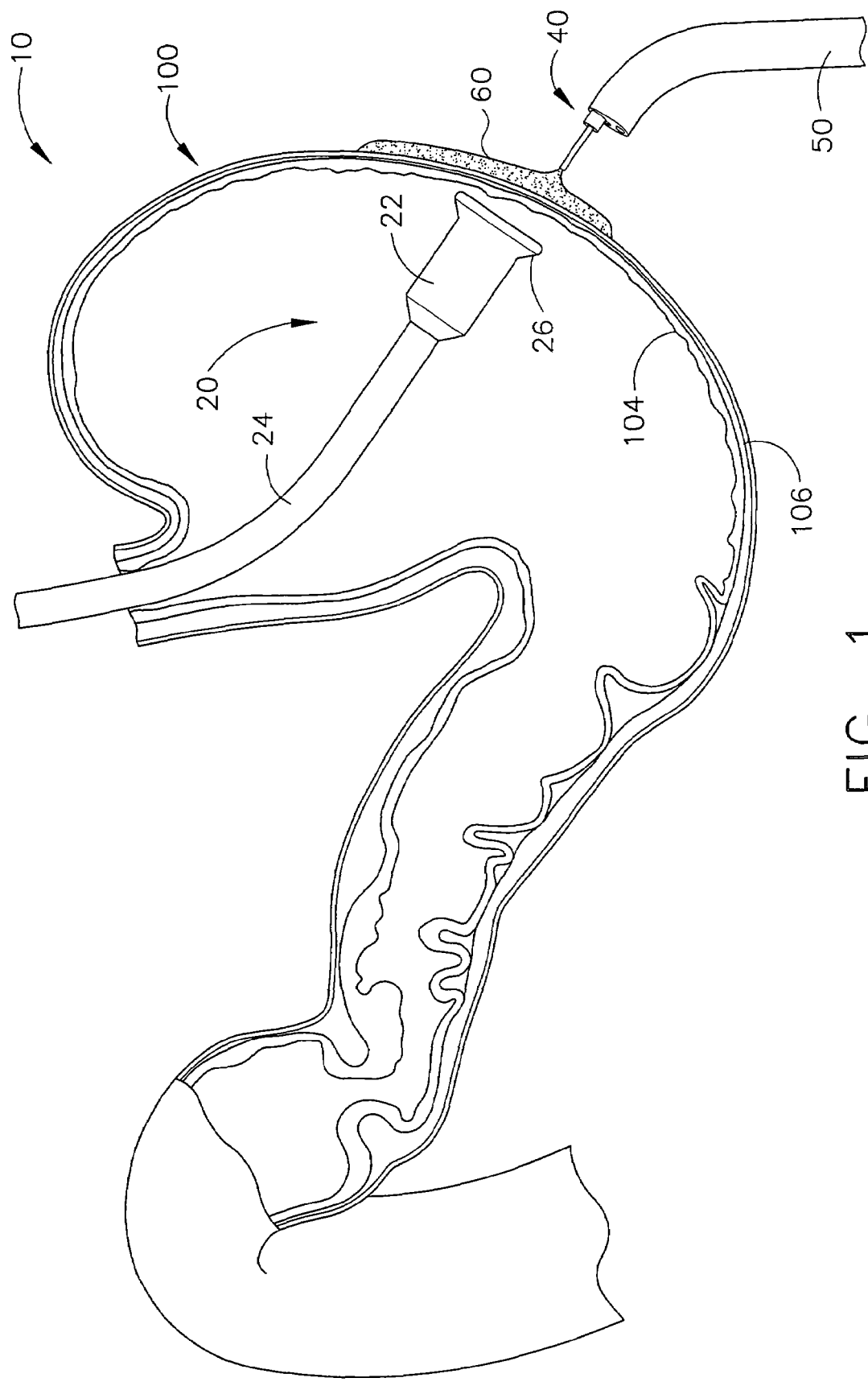
FIG. 1 depicts an exemplary suction device within a stomach, and an exemplary method for applying adhesive to an outer wall of the stomach.
Figure 2:
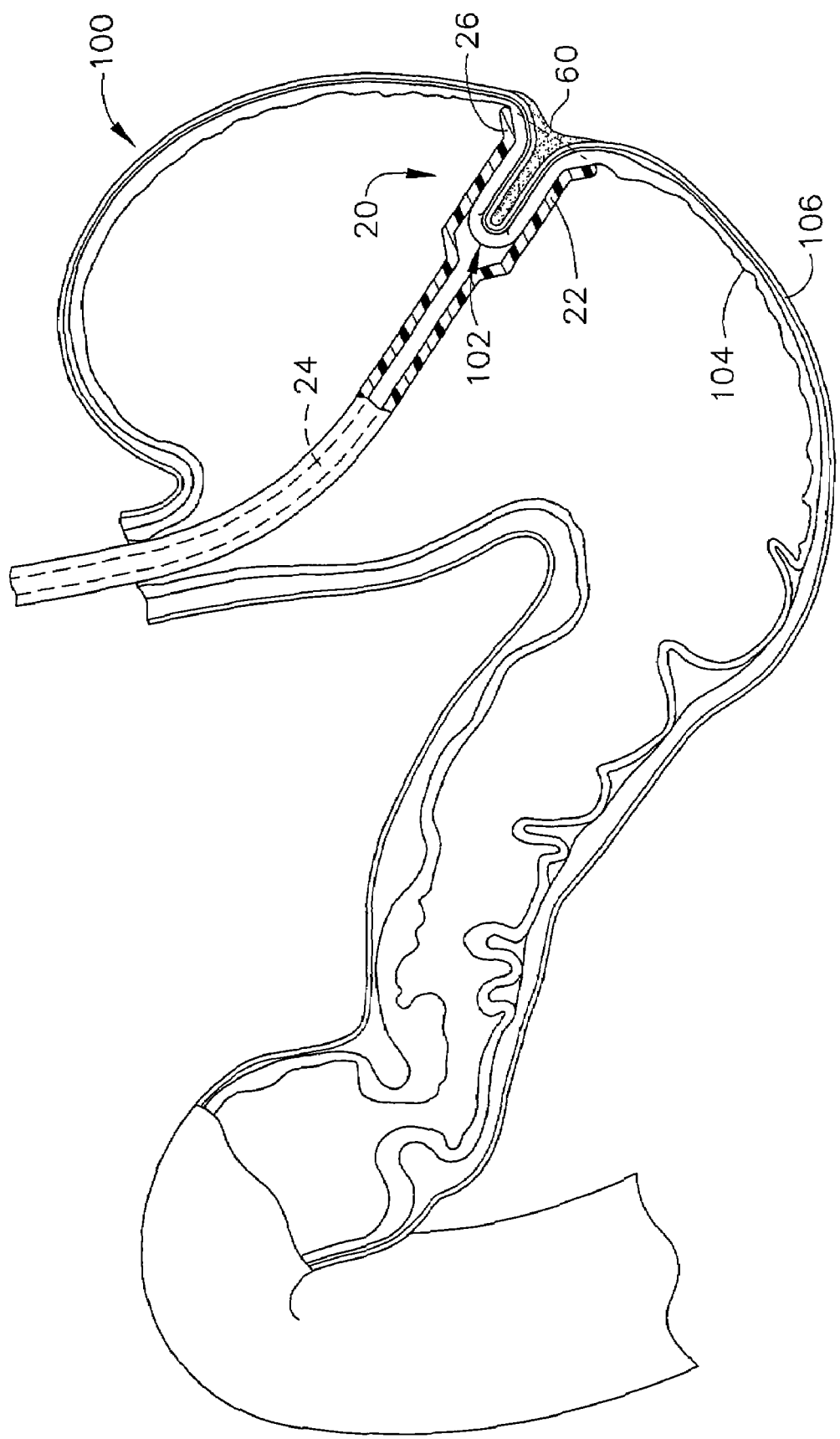
FIG. 2 depicts a partial cross-sectional view of the suction device of FIG. 1 engaged with a stomach.
Figure 3:
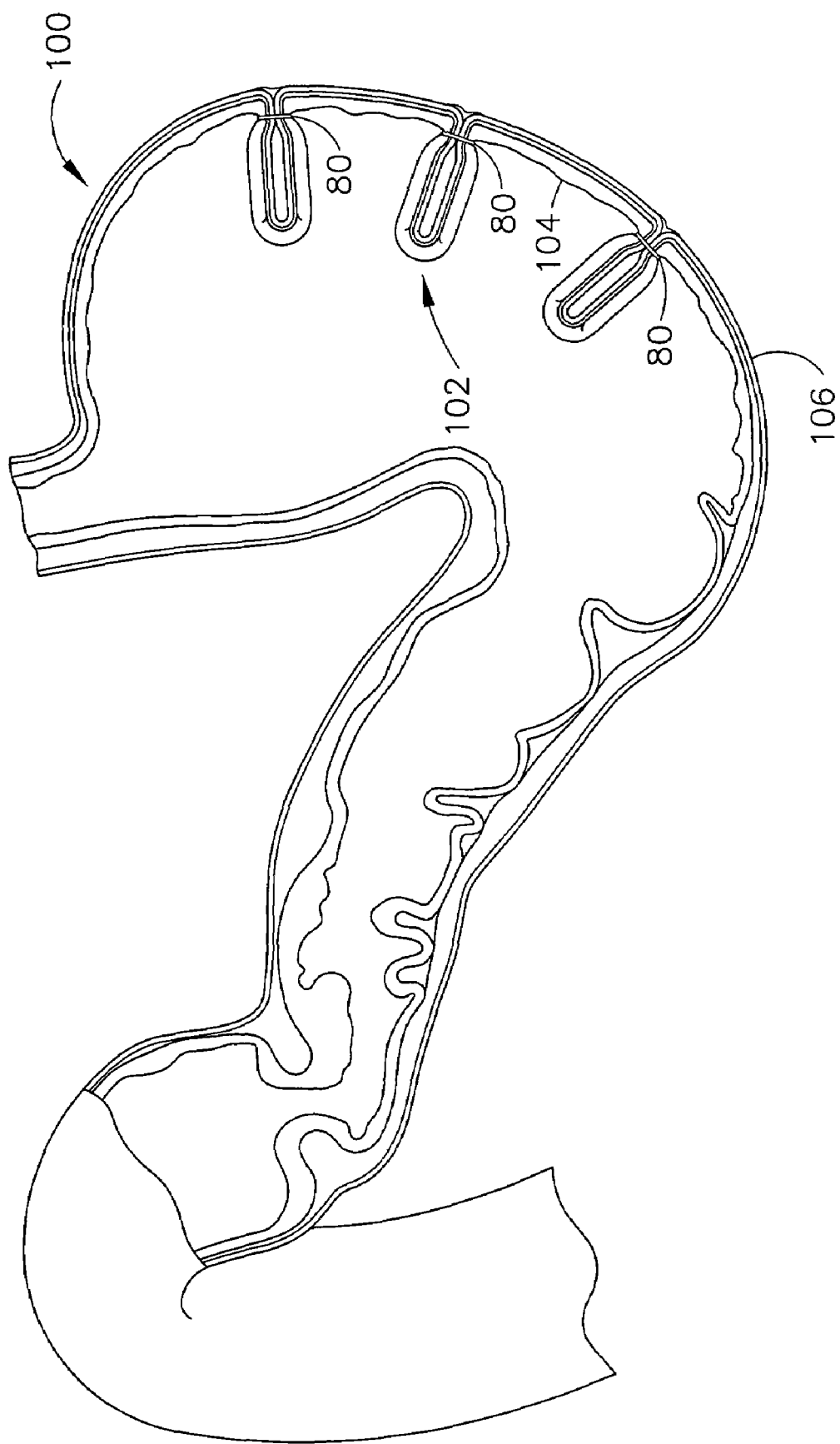
FIG. 3 depicts a cross-sectional view of exemplary invaginated stomach portions.

As shown in FIG. 1, an exemplary invagination system (10) comprises a suction device (20) and an endoscopic adhesive applier (40). In the present example, suction device (20) is disposed within a stomach (100); while adhesive applier (40) is positioned outside stomach (100). As shown in FIGS. 1-3, and as will be described in greater detail below, invagination system (10) is operable to create several invaginated portions (102) of stomach (100). The creation of such invaginated portions (102) may ultimately reduce the volume of stomach (100).

The suction device (20) comprises a head (22) coupled with a flexible tube (24). As shown head (22) has an annular, outwardly flared rim (26), and is in fluid communication with flexible tube (24). Rim (26) is configured to sealingly engage an inner stomach surface (104). As shown in FIG. 2, with rim (26) engaged with inner stomach surface (104), a vacuum may be provided through flexible tube (24) to draw a portion of stomach (100) into head (22), thereby creating an invaginated portion (102) of stomach (100). It will be appreciated that the illustrated configuration for head (22) is merely exemplary, and that head (22) may alternatively comprise a variety of alternative features and configurations.

As shown in FIG. 1, adhesive applier (40) of the present example is configured to fit within a working channel of an endoscope (50). Adhesive applier (40) in this example is a conventional endoscopic adhesive applier, though any suitable alternative may be used. Adhesive applier (40) is operable to dispense an adhesive (60) on an outer surface (106) (e.g., serosal surface) of stomach (100). Adhesive (60) may comprise a cyanoacrylate, an isocyanate, or any other suitable substance.

Figure 5:
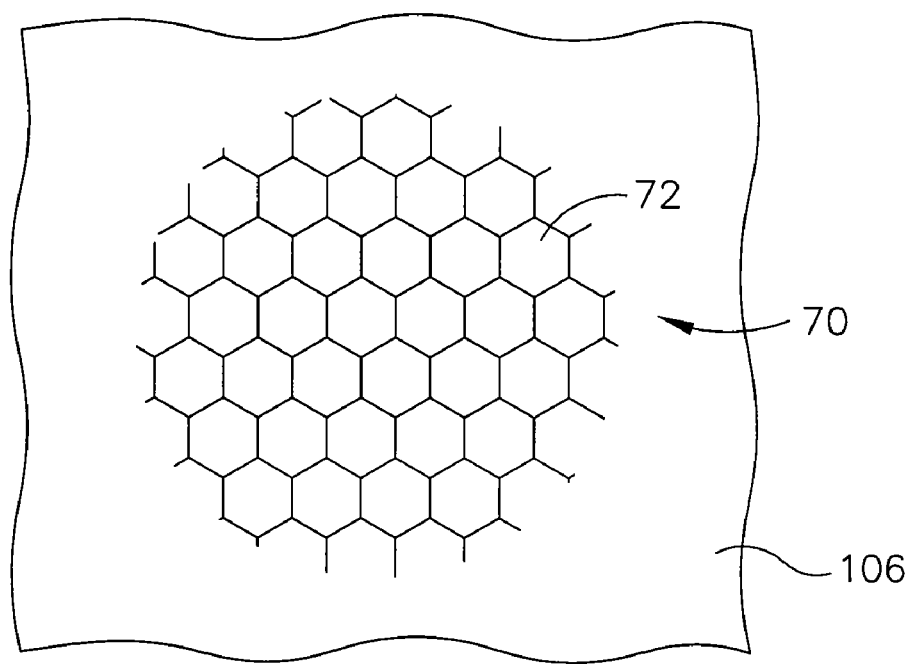
FIG. 5 depicts a plan view of an exemplary adhesive matrix applied to an outer stomach wall.

As shown in FIG. 5, in one exemplary use, a matrix cloth (70) may be applied to outer surface (106) of stomach (100) before adhesive (60) is applied. Matrix cloth (70) may comprise a plurality of cells (72), such as in a honeycomb configuration by way of example only. Each cell (72) may comprise an activator substance that is configured to react with adhesive (60). In particular, adhesive (60) may be configured such that it is not operable to satisfactorily adhere tissue unless placed in contact with the activator substance. Alternatively, matrix cloth (70) may lack an activator substance. By way of example only, to the extent a matrix cloth (70) is used, matrix cloth (70) may comprise polyester or any other suitable material or materials.

In another embodiment, matrix cloth (70) contains adhesive (60), such that a separate applier (40) is not needed to apply adhesive (60). For instance, cells (72) may contain adhesive (60). Alternatively, matrix cloth (70) material may itself be adhesive, with no adhesive (60) being provided within cells (72). In this variation, portions of matrix cloth (70) may adhere to outer surface (106) and/or to other portions of matrix cloth (70). This may permit contact between adjacent outer surface (106) portions through voids provided by empty cells (72), which may result in fusion of such adjacent outer surface portions (106). Alternatively, matrix cloth (70) may be substituted with any suitable alternative, supplemented with other structures or substances, or may be omitted altogether. To the extent that a matrix cloth (70) is used, suitable methods for applying matrix cloth (70) will be apparent to those of ordinary skill in the art.

Figure 6:
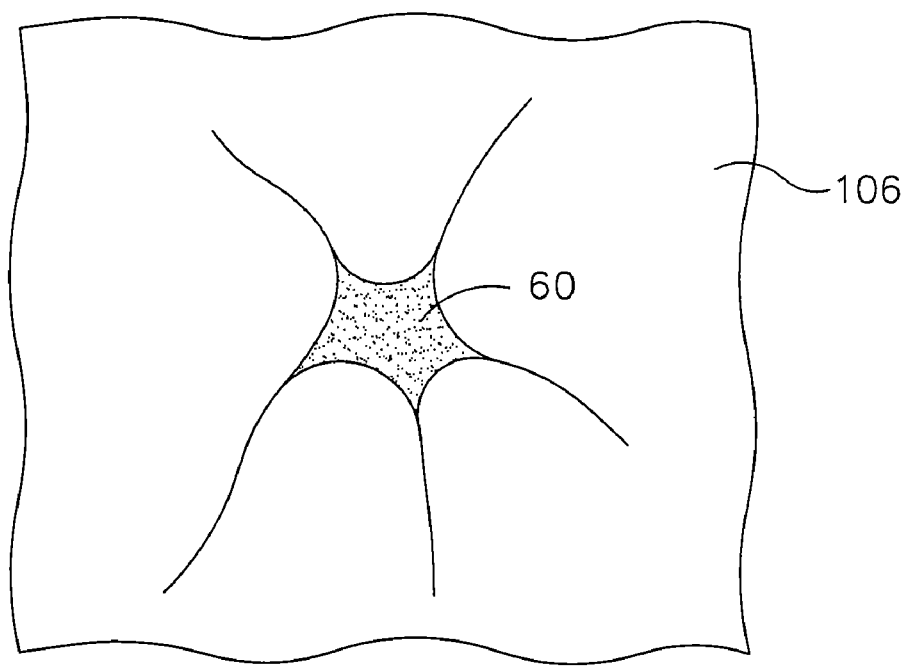
FIG. 6 depicts a plan view of the outer stomach wall of FIG. 5 after the wall has been invaginated.

In the present example, as shown in FIG. 2, head (22) is applied to stomach (100) opposite of applied adhesive (60) and matrix cloth (72). When suction is used via flexible tube (24) and head (22) to create invaginated portion (102) of stomach (100), adhesive (60) and matrix cloth (72) are also pulled in with invaginated portion (102). As shown in FIGS. 2 and 6, adhesive (60) is entrained in the interior portion of invaginated portion (102). It will be appreciated that adhesive (60) may provide sufficient adhesion to maintain the configuration of invaginated portion (102). In another embodiment, adhesive (60) is applied after invaginatied portion (102) has been created. For instance, adhesive applier (40) may be pressed into the well provided in outer surface (106) by invaginated portion (102). Adhesive (60) may be applied until it begins excreting from within the well or until otherwise desired.

In one variation, and as shown in FIG. 3, one or more sutures (80) are applied at or near the base of each invaginated portion (102) to further assist the maintenance of invaginated portion (102) configurations (and/or for other purposes). Sutures (80) may also cut of blood circulation for each invaginated portion (102), resulting in the death of tissue forming each invaginated portion (102). Of course, any suitable alternative to sutures (80) may be used, including but not limited to bands, clips, staples, etc. Alternatively, sutures (80) may be substituted, supplemented, or omitted altogether, as desired.

Figure 4:
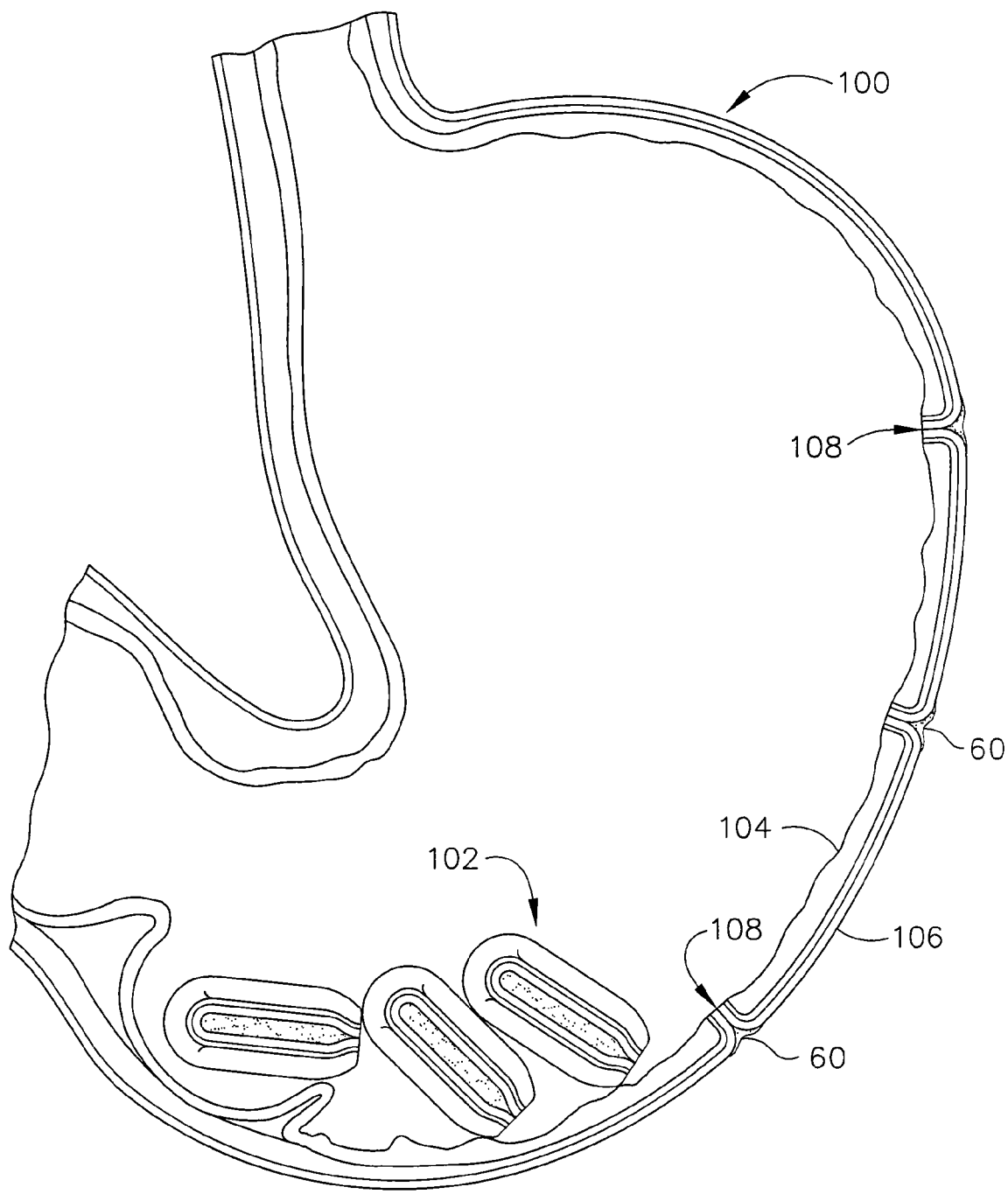
FIG. 4 depicts a cross-sectional view of the invaginated stomach portions of FIG. 3 detached from the inner stomach wall.

In one embodiment, as shown in FIG. 4 invaginated portions (102) may eventually separate from stomach (100) (e.g., after at least a portion of the tissue forming invaginated portions (102) necroses or dies). Such separated invaginated portions (102) may thereafter pass through the gastrointestinal tract. At sites (108) where each invaginated portion (102) was formerly located, a remaining amount of adhesive (60) may prevent an opening from forming through stomach (100). In addition, or in the alternative, scar tissue or other tissue fusion may prevent the formation of such openings. Ultimately, in the present example, the structural integrity of stomach (100) will be preserved despite the separation of invaginated portions (102) from their respective sites (108). It will also be appreciated that the separation of invaginated portions (102) may cause a reduction in acid producing surface. To the extent that invagination system (10) is used to treat obesity, such a reduction in acid producing surface may further provide a desirable malabsorbative result. Such a malabsorbative result may compliment reduction in stomach volume caused by invagination as a means for addressing obesity.

Figure 7:
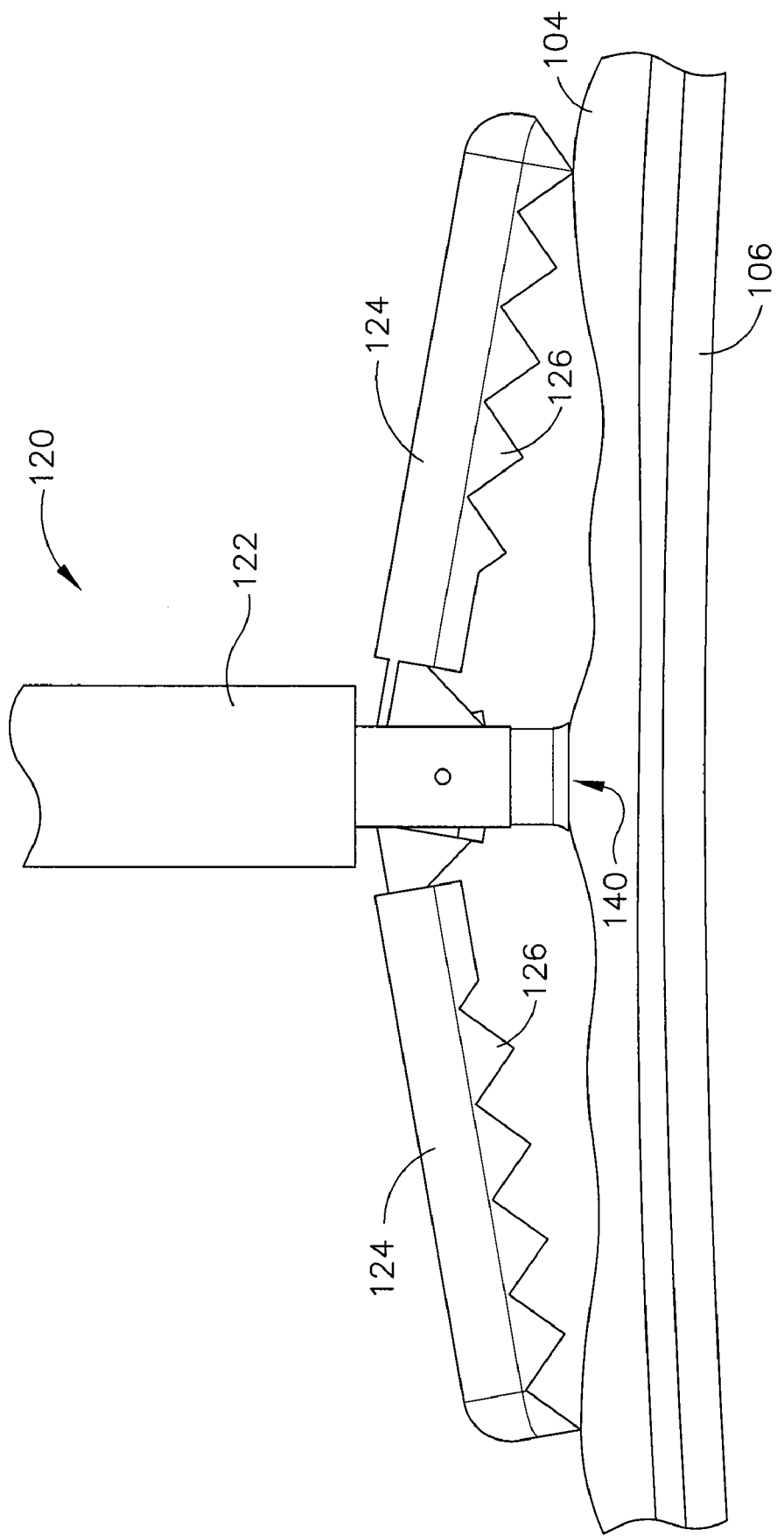
FIG. 7 depicts a partial view of an exemplary alternative invagination device.
Figure 8:
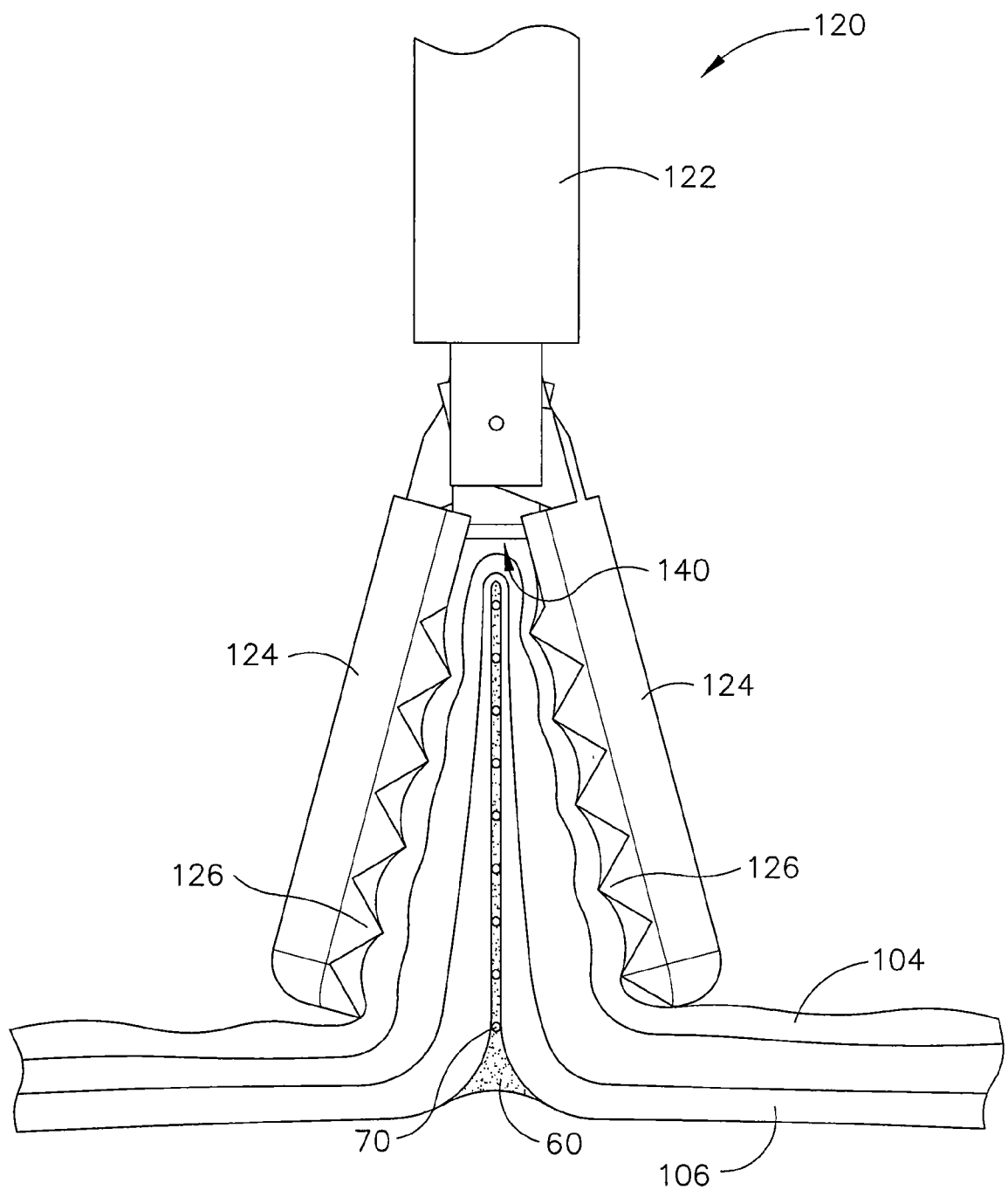
FIG. 8 depicts the invagination device of FIG. 7 performing an exemplary act of invagination.
Figure 9:
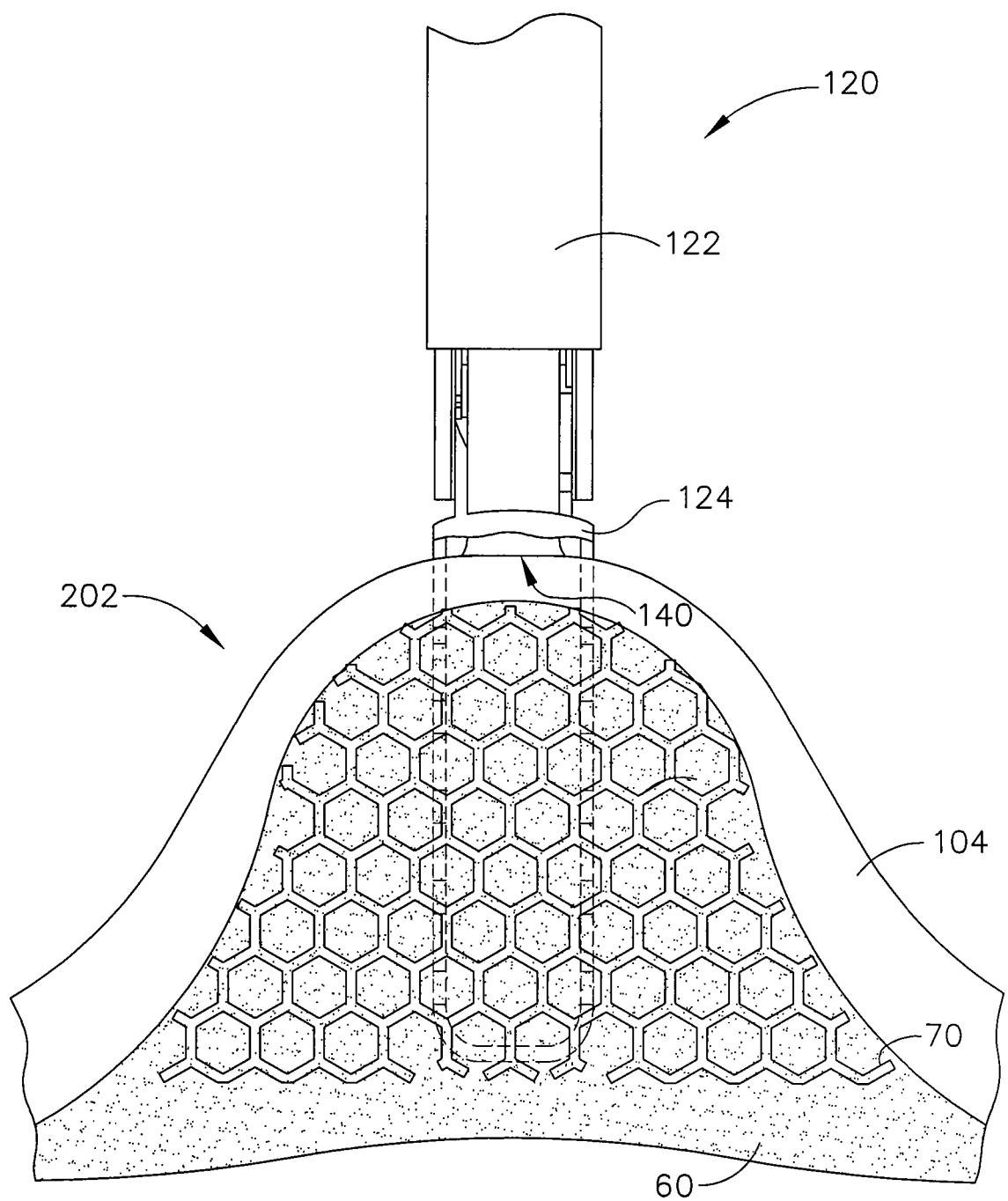
FIG. 9 depicts a partial cross-sectional view, taken along line 9-9 of FIG. 8, of the invagination device of FIG. 7 performing an exemplary act of invagination.

FIGS. 7-9 depict a gripping instrument (120) that may be used as an alternative to suction device (20). As shown, gripping instrument (120) comprises a shaft (122) and a pair of gripping jaw members (124). Shaft (122) is generally flexible, and is configured to be introduced to a patient's stomach (100) through the patient's esophagus (e.g., endoscopically, etc.). As will be described in greater detail below, shaft (122) further comprises a lumen (not shown) through which a vacuum may be provided.

Gripping jaw members (124) are pivotally connected relative to shaft (122), such that jaw members (124) may be selectively provided in an open or closed positions. Each gripping jaw member (124) has a plurality of teeth (126). Teeth (126) are configured to grip tissue, such as inner stomach surface (104). Gripping jaw members (124) may be operable to open and close via cables (not shown). Cables in the present example extend through shaft (122) to a user input device (not shown). Of course, any suitable alternative to cables may be used to open and/or close gripping jaw members (124).

Gripping instrument (120) of the present example further comprises a vacuum port (140). Vacuum port (140) may have a configuration similar to that of head (22) on suction device (20). In the present example, vacuum port (140) has a diameter that is less than the diameter of head (22) on suction device (20). Vacuum port (140) is in fluid communication with vacuum lumen of shaft (122). Vacuum port (140) may be used to secure inner stomach surface (104) relative to gripping jaw members (124), such as before gripping jaw members (124) are used to grip inner stomach surface (104).

In use, matrix cloth (70) and adhesive (60) are applied to outer stomach surface (106). Gripping instrument (120) is positioned adjacent inner stomach surface (104), substantially opposite of matrix cloth (70) and adhesive (60). With gripping jaw members (124) in an open position, vacuum is applied through vacuum port (140), securing inner stomach surface (104) relative to gripping jaw members (124), as shown in FIG. 7. Gripping jaw members (124) are then actuated to a substantially closed position while gripping inner stomach surface (104) with teeth (126), as shown in FIGS. 8-9. An invaginated portion (202) is thereby created in stomach (100). In the present example, invaginated portion (202) is similar to invaginated portion (102), except that invaginated portion (202) is generally wider in one dimension. It will therefore be appreciated that creation of invaginated portion (202) may result in greater reduction of stomach (100) volume than creation of invaginated portion (102). It will also be appreciated that the base of invaginated portion (202) may be further secured with one or more sutures, bands, clips, staples, etc.

Figure 10:
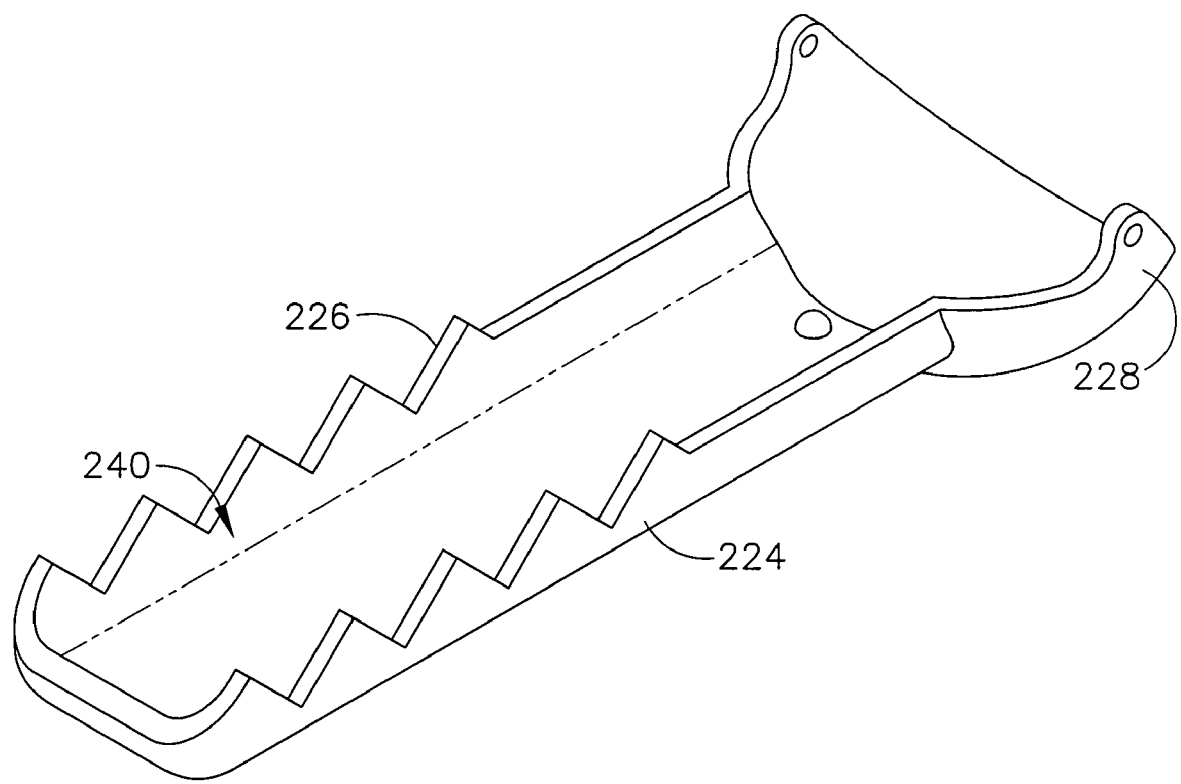
FIG. 10 depicts a perspective view of an exemplary alternative gripping jaw member.
Figure 11:
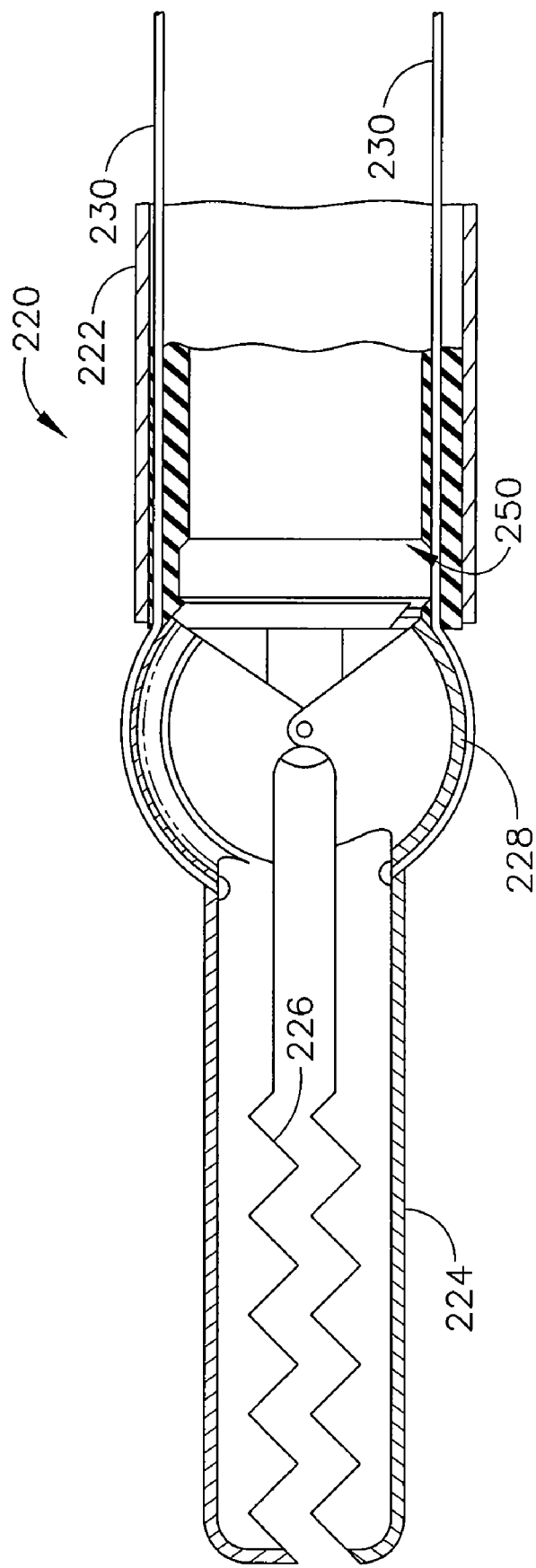
FIG. 11 depicts a partial cross-sectional view of an exemplary alternative invagination device with the gripping jaw member of FIG. 10.
Figure 12:
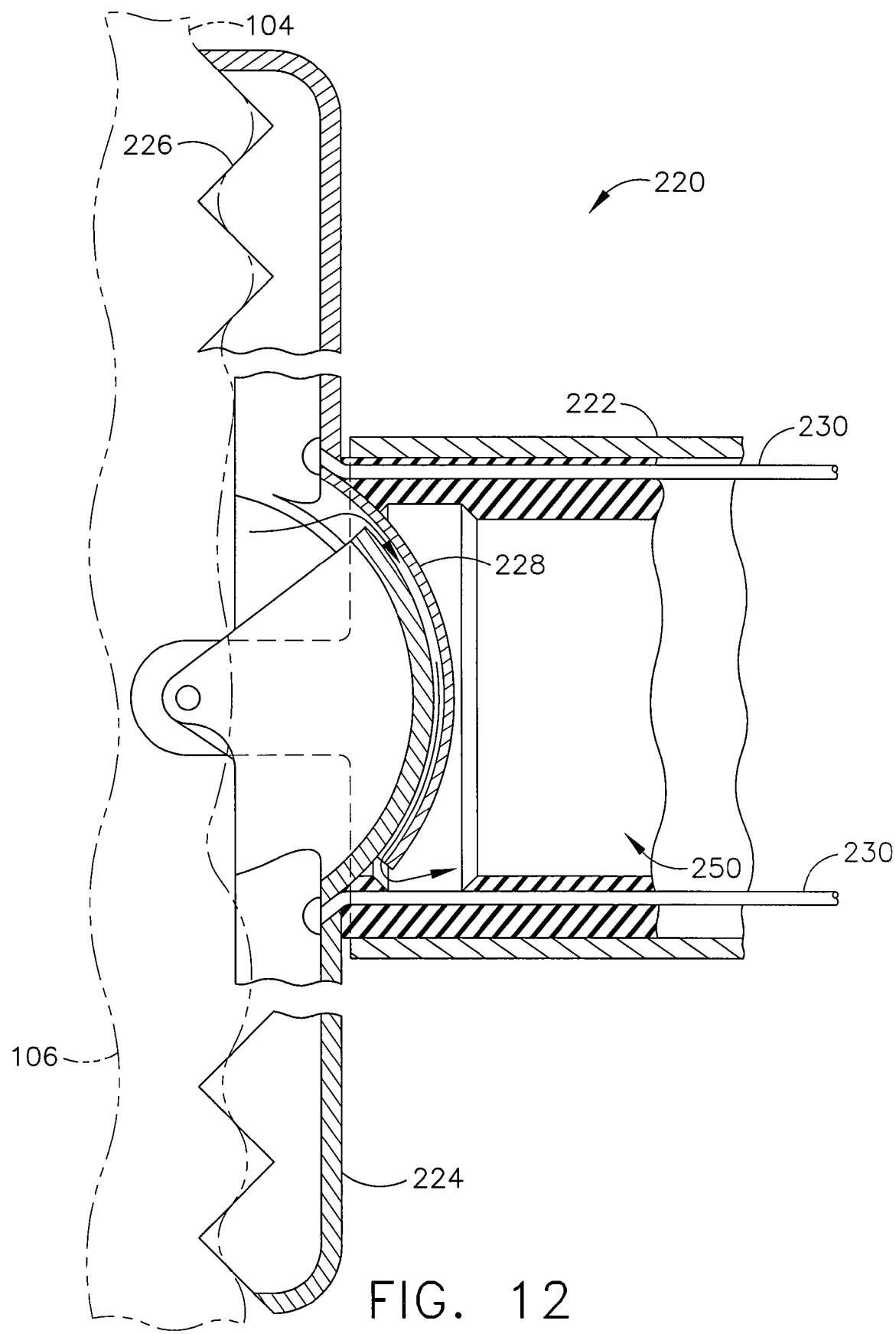
FIG. 12 depicts a partial cross-sectional view of the device of FIG. 11 with the gripping jaw members in a generally open position.

An exemplary variation of gripping instrument (120) is shown in FIGS. 10-12. In this variation, gripping instrument (220) comprises a shaft (222) and a pair of gripping jaw members (224). Shaft (222) is generally flexible, and is configured to be introduced to a patient's stomach (100) through the patient's esophagus (e.g., endoscopically, etc.). As will be described in greater detail below, shaft (222) further comprises a lumen (250) through which a vacuum may be provided.

Gripping jaw members (224) are pivotally connected relative to shaft (222), such that jaw members (224) may be selectively provided in an open or closed positions. Each gripping jaw member (224) has a plurality of teeth (226). Teeth (226) are configured to grip tissue, such as inner stomach surface (104). Gripping jaw members (224) may be operable to open and close via cables (230). Cables (230) in the present example extend through shaft (222) to a user input device (not shown). Of course, any suitable alternative to cables (230) may be used to open and/or close gripping jaw members (224).

Each gripping jaw member (224) comprises a generally spherically-shaped joint portion (228). Joint portions (228) are configured to overlap within shaft (222) while gripping jaw members (224) are in an open position. Each gripping jaw member (224) also has a cup-like configuration, which is configured to provide a vacuum chamber (240). Such vacuum chambers (240) are in fluid communication with lumen (250), such that a vacuum may be provided within vacuum chambers (240) via lumen (250). In another variation, a cover (not shown) having a plurality of apertures is provided over each vacuum chamber (240). Alternatively, any other structural variation of gripping jaw members (224) may be used.

While lumen (250) is depicted as generally being the interior of shaft (222), it will be appreciated that lumen (250) may alternatively be provided by a separate member (not shown) inserted through shaft (222). Other structural variations will be apparent to those of ordinary skill in the art.

In an exemplary use, gripping instrument (220) is used in a manner similar to the use of gripping instrument (120) described above. However, instead of suction being provided through vacuum port (140), suction is provided through vacuum chambers (240) of gripping jaw members (224). Such suction may be provided before and during the gripping of inner stomach surface (104) of teeth (226), and may assist teeth (226) in the gripping of inner stomach surface (104). Suction may continue to be provided as gripping jaw members (224) are brought to a closed position, whereupon an invaginated portion (202) is created.

As will be appreciated by those of ordinary skill in the art, the creation of invaginated portions (102, 202) may result in a reduction of stomach (100) volume. Such reduction in stomach (100) volume may (or may not) provide a method for treating morbid obesity in a patient, and/or may provide other results. Other suitable structural variations of suction device (20) and gripping instruments (120, 220), as well as variations of uses for the same, will be apparent to those of ordinary skill in the art.

It will be appreciated that the invagination systems (10) described herein, including variations of the same, may be used in laparascopic, endoscopic, open, and/or other surgical settings, including combinations thereof.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A system for creating an invaginated portion in a stomach, the system comprising:
   (a) a suction device, wherein the suction device comprises:
      (i) a suction head operable to provide suction,
      (ii) a shaft, wherein the suction head is connected to the shaft,
      (iii) a vacuum lumen positioned within the shaft and in fluid communication with the suction head,
         wherein the suction device is configured for the suction head to be placed adjacent to tissue inside a patient's stomach, wherein the suction head and vacuum lumen are operable to induce a vacuum adjacent to the tissue, wherein the suction device is further operable to create an invaginated portion with the tissue, and
      (iv) a plurality of gripping jaw members that extend from the shaft of the suction device, each of the gripping jaw members having a cup-like configuration and further comprising a joint portion defining a generally spherically-shaped concavity, the concavity of a first joint portion being complementary to the concavity of a second joint portion, wherein the gripping jaw members are operable to be placed in an open position or a closed position by being pivotable about the joint portions, and wherein at least part of the complementary generally spherically-shaped concavities of the joint portions overlap within the shaft when the gripping jaw members are in an open position, and wherein the cup-like configuration of each of the gripping jaw members provides a vacuum chamber in fluid communication with the vacuum lumen such that a vacuum can be provided within the vacuum chamber through the lumen; and
   (b) a securing member, wherein the securing member is operable to substantially maintain the configuration of the invaginated portion of tissue, wherein the securing member comprises an adhesive positioned on the exterior surface of the patient's stomach.

2. The system of claim 1, wherein the suction head has an annular, outwardly flared rim.

3. The system of claim 1, wherein the suction device further comprises a vacuum port positioned near the gripping jaw members.

4. The system of claim 1, wherein the adhesive comprises one or both of a cyanoacrylate or an isocyanate.

5. The system of claim 1, wherein the securing member further comprises an activator configured to activate the adhesive.

6. The system of claim 5, wherein the securing member further comprises a matrix, wherein the activator is provided within the matrix.

7. The system of claim 1, wherein the securing member comprises one or more of a suture, a staple, or a clip.

8. The system of claim 1, wherein the securing member is configured to be applied endoscopically.

9. The system of claim 1, wherein the shaft has an interior wall, wherein the vacuum lumen is provided by the interior wall of the shaft.

10. A system for creating an invaginated portion in a stomach, the system comprising:

(a) a means for inducing a vacuum adjacent tissue;
(b) a means for creating an invaginated portion of the tissue, wherein the means for creating an invaginated portion is configured to be introduced into the interior of a patient's stomach, wherein the means for creating an invaginated portion is configured to be actuated to engage tissue inside the patient's stomach, wherein the means for creating an invaginated portion is configured to appose two portions of the exterior surface of the patient's stomach; and
(c) a means for maintaining the configuration of the invaginated portion of the tissue created by the means for creating an invaginated portion, wherein the means for maintaining the configuration comprises an adhesive applied to the two portions of the exterior surface of the patient's stomach;
wherein when the means for inducing a vacuum and the means for creating an invaginated portion of the tissue is placed adjacent to the tissue inside the stomach and opposite the two portions of the exterior surface of the stomach having the adhesive applied thereon, and a vacuum is induced adjacent to the tissue, and the means for creating an invaginated portion of the tissue is actuated, an invaginated portion of the stomach is created with the adhesive positioned on the two portions of the exterior surface of the stomach being drawn into the invaginated portion to promote adhesion between the two apposed exterior surfaces of the patient's stomach.

11. A system for creating an invaginated portion in a stomach, wherein the stomach comprises an inner portion and an outer portion opposite the inner portion, the system comprising:

(a) a suction device comprising a vacuum port, a shaft extending from the vacuum port, a lumen in fluid communication with the shaft, and a suction head having an annular, outwardly flared rim in fluid communication with the lumen; and
(b) an adhesive applier, wherein the adhesive applier is configured to be positioned proximate to the outer portion of the stomach, wherein the adhesive applier is operable to apply adhesive to the outer portion of the stomach;
wherein the vacuum port and suction head are configured to be positioned proximate to the inner portion of the stomach, wherein the rim of the suction head is configured to sealingly engage the inner portion of the stomach, wherein the vacuum port and lumen are operable to induce a vacuum adjacent to the inner portion of the stomach to cause part of the inner portion of the stomach to be drawn into the vacuum port of the suction device, thereby apposing parts of the outer portion of the stomach and causing the adhesive applied to the outer portion of the stomach to be sandwiched in between the apposing parts to promote adhesion between the apposed parts of the outer portion of the stomach.

12. The system of claim 11, further comprising a matrix cloth configured to be positioned between the apposed parts of the outer portion of the stomach.

13. The system of claim 12, wherein the matrix cloth is configured to react with the adhesive, wherein the adhesive is operable to adhere the apposed parts of the outer portion of the stomach when the adhesive is placed in contact with the matrix cloth.

* * * * *